United States Patent [19]
Mulhauser et al.

[11] Patent Number: 5,919,167
[45] Date of Patent: Jul. 6, 1999

[54] DISPOSABLE MICROPUMP

[75] Inventors: Paul J. Mulhauser, New York, N.Y.;
Diego Y. Fontayne, Teaneck, N.J.;
Donald F. VanRoyen, New York, N.Y.

[73] Assignee: Ferring Pharmaceuticals, Keil, Germany

[21] Appl. No.: 09/056,751

[22] Filed: Apr. 8, 1998

[51] Int. Cl.⁶ .................................................. A61M 37/00
[52] U.S. Cl. ............................................................ 604/131
[58] Field of Search .................................. 604/131, 154, 604/155, 151

[56] References Cited

U.S. PATENT DOCUMENTS

| | | |
|---|---|---|
| 2,722,613 | 11/1955 | Culbertson et al. . |
| 4,018,547 | 4/1977 | Rogen . |
| 4,551,975 | 11/1985 | Yamamoto . |
| 4,585,439 | 4/1986 | Michel . |
| 4,755,172 | 7/1988 | Baldwing .............................. 604/131 |
| 4,883,472 | 11/1989 | Michel . |
| 4,931,041 | 6/1990 | Faeser . |
| 5,222,362 | 6/1993 | Maus et al. . |
| 5,507,727 | 4/1996 | Crainich . |
| 5,618,269 | 4/1997 | Jacobsen et al. ....................... 604/131 |
| 5,637,095 | 6/1997 | Nason et al. ............................ 604/154 |

*Primary Examiner*—Jeffrey A. Smith
*Assistant Examiner*—Eduardo C. Robert
*Attorney, Agent, or Firm*—Pennie & Edmonds LLP

[57] ABSTRACT

An apparatus for delivery of a fluid is disclosed. The apparatus includes a syringe pump with a plunger, an electronic control element which releases at least one electric charge at predetermined time intervals, a shape memory element with a contractible length decreasing from an uncharged length to a charged length, and a driving mechanism connected to both the shape memory element and the plunger so that the change in length of the shape memory element causes the driving mechanism to provide an activating force to move the plunger and force the expulsion of the fluid from the syringe pump's chamber. As the apparatus according to the present invention can be manufactured as a disposable unit, the problems associated with reusable syringe pumps are avoided.

16 Claims, 4 Drawing Sheets

5,919,167

DISPOSABLE MICROPUMP

FIELD OF THE INVENTION

The invention relates generally to an apparatus for delivery of a liquid, and more particularly to a disposable, pulsatile micropump for infusion.

BACKGROUND OF THE INVENTION

The use of a syringe pump for infusion of medicament is well known. In a syringe pump, an activating force causes the movement of a plunger to expel fluid from the pump's chamber. Typically, an electric motor provides the activating force. For example, U.S. Pat. No. 4,585,439 discloses a portable infusion unit driven by a motor. The unit is configured so that once all the medicament has been used from an injection ampule, another injection ampule can be inserted in the unit. The motor increases the weight and size of the unit. Smaller motors are available. However, irrespective of size, the inclusion of a motor increases manufacturing costs and makes the design of a disposable, single-use unit unrealistic.

There are other disadvantages to reusable syringe pumps. The batteries powering the electric motor need to be either replaced or recharged. Even if a motor is not used to drive the plunger, the maintenance associated with a reusable device can be troublesome.

Thus, there exists a need for an improved apparatus for delivery of a fluid.

SUMMARY OF THE INVENTION

The apparatus according to the invention comprises a syringe pump with a plunger, an electronic control element which releases at least one electric charge at predetermined time intervals, a power source for providing electrical energy to the electronic control element, a shape memory element that decreases in length from an uncharged length to a charged length when a charge is applied and, under the force of a return spring, returns to the uncharged length when the charge is removed, and a driving mechanism connected to both the shape memory element and the plunger so that the change in length of the shape memory element causes the driving mechanism to provide an activating force to move the plunger and force the expulsion of fluid from the syringe pump chamber.

In one embodiment, the driving mechanism includes a power screw attached to the plunger, a fixed nut through which the power screw is threaded, a coupler having a bore for receiving the power screw, a pawl which moves from a resting position when the shape memory element has the uncharged length to an actuating position when the shape memory element has the charged length, and a return spring for returning the pawl to the resting position and the shape memory element to the uncharged length. The movement of the pawl causes the rotation of the coupler and the power screw and the rotation of the power screw through the nut causes longitudinal movement of the power screw to provide the activating force. The plunger has a bottom end configured such that substantially all of the fluid is expelled from the chamber when the bottom end contacts the end of the chamber and a side surface containing one or more seals contacting the chamber interior wall.

In a preferred embodiment, the power screw has two threadless flat parallel surfaces and two threaded curved surfaces and the bore has two threadless flat parallel surfaces. The first end of the pawl preferably has a channel to which the shape memory element is secured and a projection for engaging a limiting switch to stop the charge and the second end of the pawl has a raised portion with a circular opening for receiving the coupler and an extension with a tab that engages a ratchet on an external surface of the coupler to initiate the rotation of the coupler. A spring strip ratchet preferably engages teeth of the ratchet to permit rotation of the coupler in one direction only. The external surface of the coupler has a grooved portion for manual rotation of the coupler.

In another embodiment, the syringe pump chamber is made of an injected molded thermoplastic polymer and the shape memory element is made of a nickel-titanium alloy.

In another embodiment, the power source is at least one battery and the electronic control element includes at least one capacitor for storing and releasing the charge and a time element for allowing the user to select a number of charges to be released and an interval at which the charges are released.

According to a final embodiment, the apparatus has a housing for retaining all components therein. Preferably, the housing includes a window to facilitate monitoring of the amount of fluid in the syringe pump.

BRIEF DESCRIPTION OF THE DRAWINGS

Additional features of the invention are provided in the following detailed description of the preferred embodiments and drawing and figures wherein.

DETAILED DESCRIPTION OF THE PREFERRED EMBODIMENTS

Figure 1:
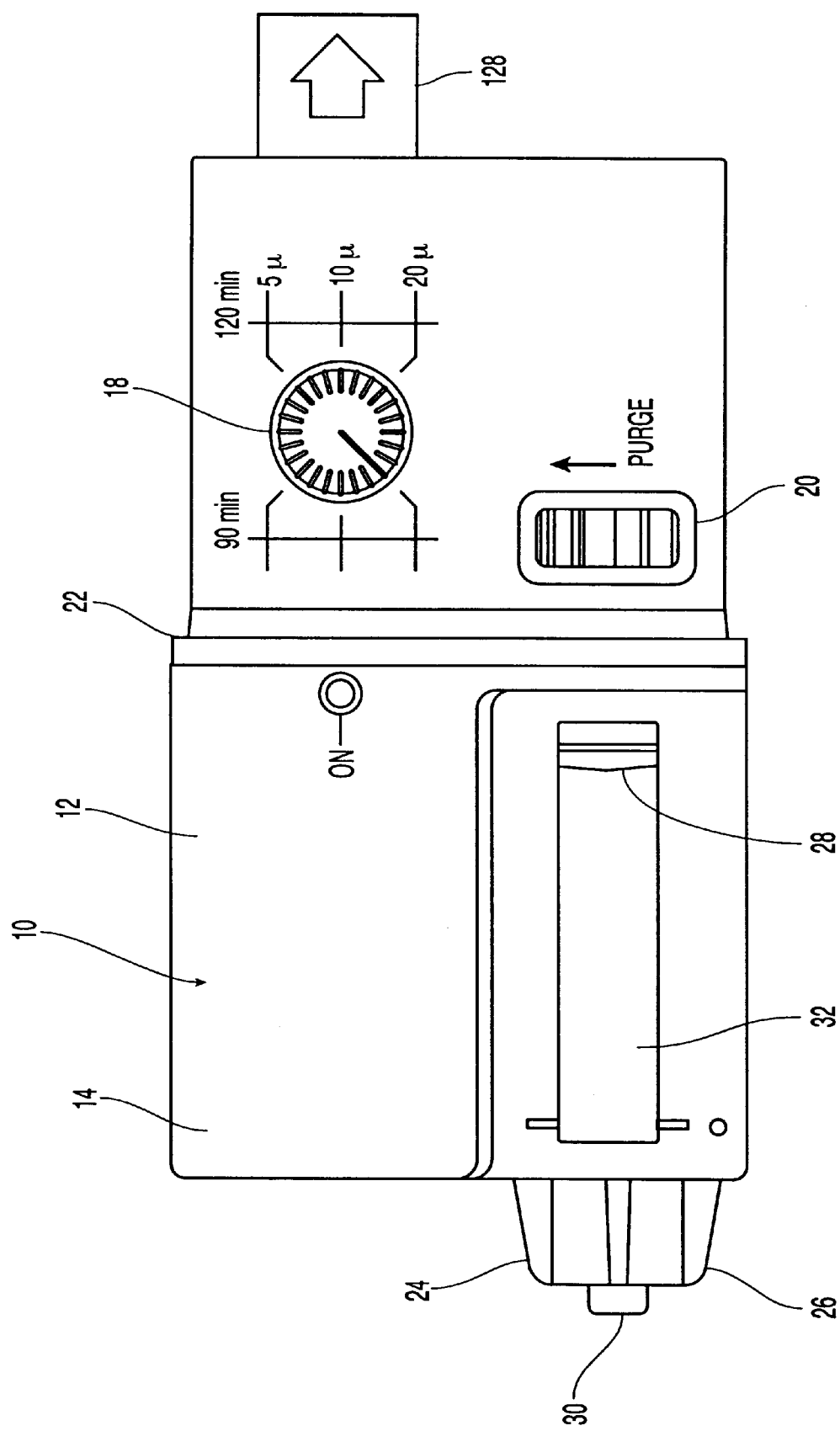
FIG. 1 is a top view of a micropump according to the invention.

FIG. 1 generally shows micropump 10. Micropump 10 has a housing 12. Housing 12 is made of a material, such as a plastic, that is waterproof. Housing 12 preferably comprises a top shell 14 and a bottom shell 16 (shown in FIG. 2). Top shell 14 and bottom shell 16 are joined together such that the junction between them is water-tight. FIG. 1 shows housing 12 without a removable cover that covers control knob 18 and purge knob 20. A gasket 22 is provided for making the interface between housing 12 and the removable cover water-tight. The need for housing 12 to be impermeable to water is desirable so that micropump 10 can retain functionality even if gotten wet, as would be the case if a user wore micropump 10 while taking a shower.

Protruding from a side of micropump 10 is a nozzle 24 of syringe pump 26. Syringe pump 26 contains a fluid (not shown) that is to be dispensed. As is the case with a conventional syringe, dispensing of fluid occurs when the linear movement of a plunger 28 of syringe pump 26 forces the fluid out a hole 30. Housing 12 includes a window 32 for viewing the position of plunger 28 and the volume of fluid remaining in syringe pump 26.

Figure 2:
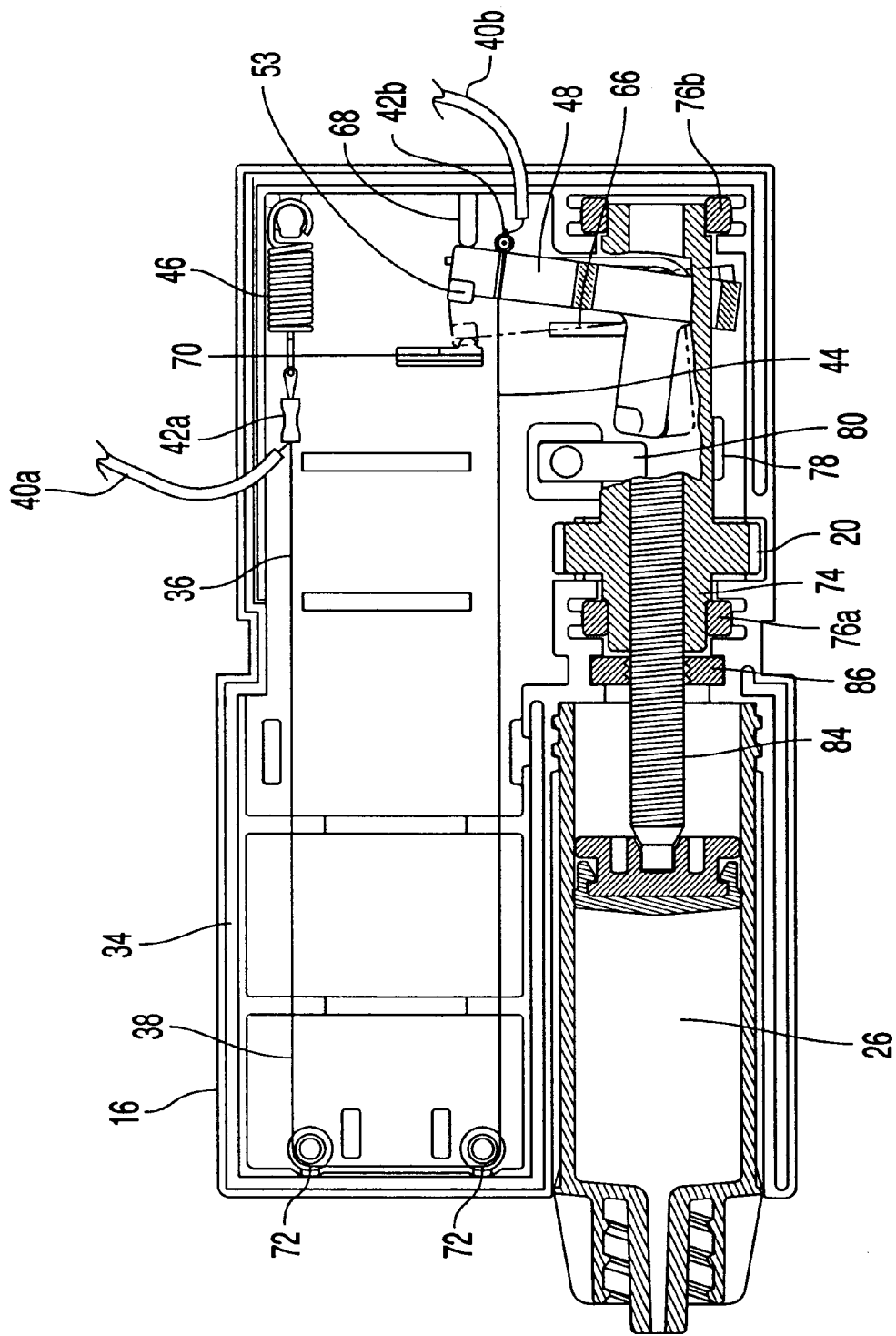
FIG. 2 is a top view of the bottom shell of the housing with the top shell removed.

Referring now to FIG. 2, bottom shell 16 is shown having a lap joint 34 that forms part of the water-tight junction between bottom shell 16 and top shell 14. One end 36 of a shape memory element 38 is connected to wire 40a by crimp 42a and another end 44 of shape memory element 38 is connected to wire 40b by crimp 42b. Crimp 42a also attaches end 36 of shape memory element 38 to an end of overload spring 46. The other end of overload spring 46 is rigidly connected to the housing 12. Crimp 42b also attaches end 44 of shape memory element 38 to a pawl 48.

Figure 3:
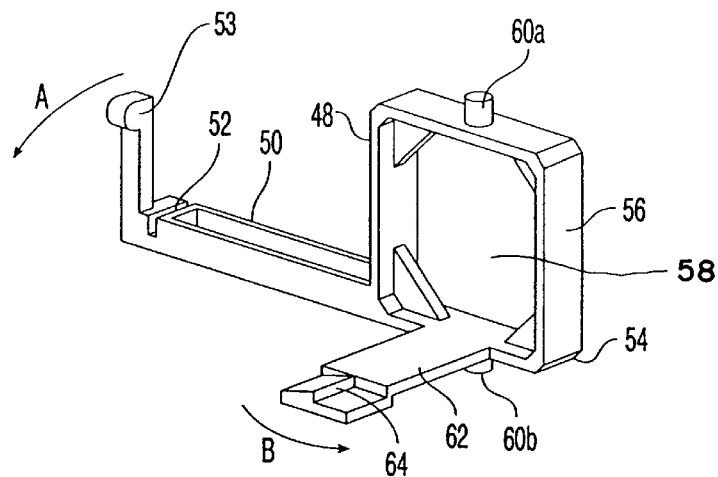
FIG. 3 is a side view of the pawl.

As shown in FIG. 3, pawl 48 has a first end 50 that includes a channel 52 for receiving end 44 of shape memory element 38 and, as discussed in more detail below, a projection 53 for interacting with an element of top shell 14 for limiting the movement of pawl 48. A second end 54 of pawl 48 has a raised portion 56. Raised portion 56 has a opening 58 and nubs 60a and 60b which pivotally connect pawl 48 to top and bottom shells 14, 16, respectively. An extension 62 has a tab 64 and extends perpendicularly to raised portion 56. As pawl 48 is pivotally connected to housing 12 by nubs 60a and 60b, movement of first end 50 in the direction of arrow A results in pawl 48 pivoting and therefore causes movement of extension 62 in the direction of arrow B. Note that arrow A and arrow B are substantially perpendicular. FIG. 2 shows pawl 48 in a resting position. A return spring 66 ordinarily maintains pawl 48 in the resting position in contact on one side with stopper 68.

Shape memory element 38 is made of a shape memory material. The application of an electrical current to a shape memory material results in molecular and crystalline restructuring of the shape memory material. If the shape memory material is in the shape of a wire, for example, as shape memory element 38 preferably is, this restructuring causes a decrease in length. After the electrical current is removed, the shape memory material returns to its original molecular and crystalline structure by being indirectly pulled and returned to its original length by return spring 66. Thus, upon application of electrical current, the wire contracts or shrinks, but then returns to its original length after the current is removed. Nitinol, a well-known alloy of nickel and titanium, is an example of such a so-called shape memory material and is preferred for use as shape memory element 38.

When a charge is applied to shape memory element 38 through wires 40a, 40b, the length of shape memory element 38 decreases from an uncharged length to a charged length. The decrease in length occurs with a force that is sufficient to overcome the biasing of pawl 48 in the resting position by return spring 66 and results in movement of pawl 48 from the resting position to an actuating position. The movement of pawl 48 occurs because overload spring 46, a tension spring, is rigidly attached to housing 12 while pawl 48 is pivotally attached to housing 12. As a result, once return spring 66 is overcome (which occurs before overload spring 46 is overcome), shape memory element 38 is free to slide along rollers 72 and pawl 48 moves from the resting position to the actuating position. Overload spring 46 prevents shape memory element 38 from breaking under the length constriction when charged. Thus, overload spring 46 keeps pawl 48 from moving further than the actuating position.

Figure 7:
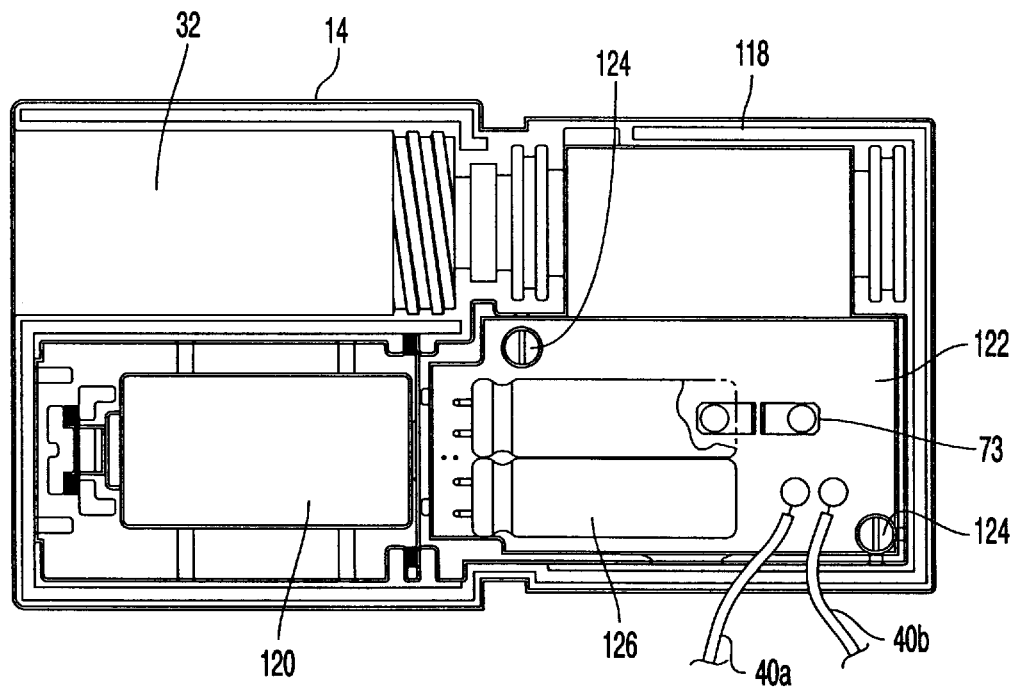
FIG. 7 is a top view of the top shell of the housing with the bottom shell removed.

Preferably, there are other mechanisms that prevent pawl 48 from moving beyond the actuating position. Specifically, when pawl 48 moves to the actuating position, projection 53 engages a limiting switch 73 (FIG. 7) to stop the application of the charge to shape memory element 38. As an alternative embodiment, projection 53 can be positioned on overload spring 46 rather than pawl 48 so that when overload spring 46 changes length, projection 53 triggers limiting switch 73. Limiting switch 73 is shown in FIG. 7 as two metallic tabs that flex to contact each other under the force of projection 53. However, any other configuration that would results in the stoppage of current when pawl 48 reaches the actuating position could be used for limiting switch 73. Movement beyond the actuating position is also prevented by forward stopper 70.

The movement of pawl 48 from the resting position to the actuating position causes a coupler 74 to rotate in the counter-clockwise direction. Rotation of coupler 74 is possible because coupler is attached to housing 12 by front and back bearing bushings 76a and 76b, respectively. The rotation results from coupler 74 being inserted in opening 58 of raised portion 56 and tab 64 engaging a ratchet 78 on the external surface of coupler 74. Manual rotation of coupler 74 is possible because purge knob 20 is actually a portion of coupler 74 with an enlarged exterior diameter and grooves to accommodate the fingers of a user. Spring strip ratchet 80 prevents clockwise rotation of coupler 74.

Figure 4:
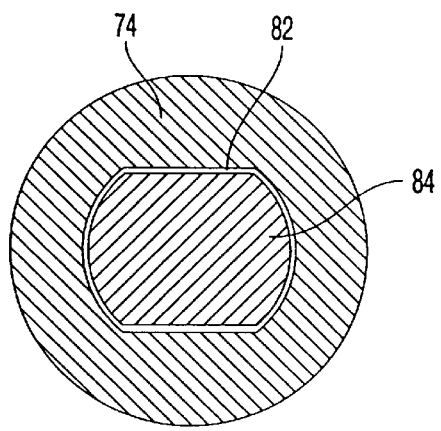
FIG. 4 is a cross-sectional view of the coupler and the power screw.
Figure 5:
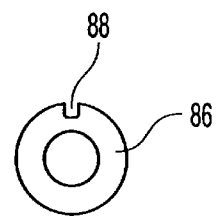
FIG. 5 is a top view of the nut.

As shown in FIG. 2 and FIG. 4, coupler 74 has a bore 82 for receiving a power screw 84. Power screw 84 has two threadless flat parallel surfaces and two curved surfaces. The curved surfaces are threaded. The bore is similarly configured, but none of the bore surfaces has threads. Because of the similar configuration and close fitting between bore 82 and power screw 84, rotation of coupler 74 results in rotation of power screw 84. Power screw 84 protrudes from bore 82 and passes through a fixed nut 86. As shown in FIG. 5, the exterior surface of nut 86 has a slot 88 which fits into a protuberance that has been molded into top shell 14 to prevent movement or rotation of nut 86. If desired, a second slot may also be provided opposite slot 88. If this were the case, bottom shell 16 would also have a protuberance to mate with the second slot. The prevention of rotation of nut 86 results in longitudinal movement of power screw 84 through nut 86 upon rotation of coupler 74 and power screw 84. Because of the attachment of power screw 84 to plunger 28, the linear movement of power screw 84 causes the linear movement of plunger 28, and hence, the expulsion of fluid from hole 30. The quantity of fluid dispensed is proportional to the amount of linear movement of plunger 28.

As previously discussed, the application of an electrical current to shape memory element 38 results in a change of length of that element. When the pulse of charge ends, the length of shape memory element 38 returns to the uncharged length by force of return spring 66 until pawl 48 rests against stopper 68. In so doing, shape memory element 38 slides along rollers 72. Even though the movement of pawl 48 from the resting position to the actuating position results in the counter-clockwise rotation of coupler 74, spring strip ratchet 80 prevents the clockwise rotation of coupler 74 when pawl 48 returns to the resting position from the actuating position.

Figure 6:
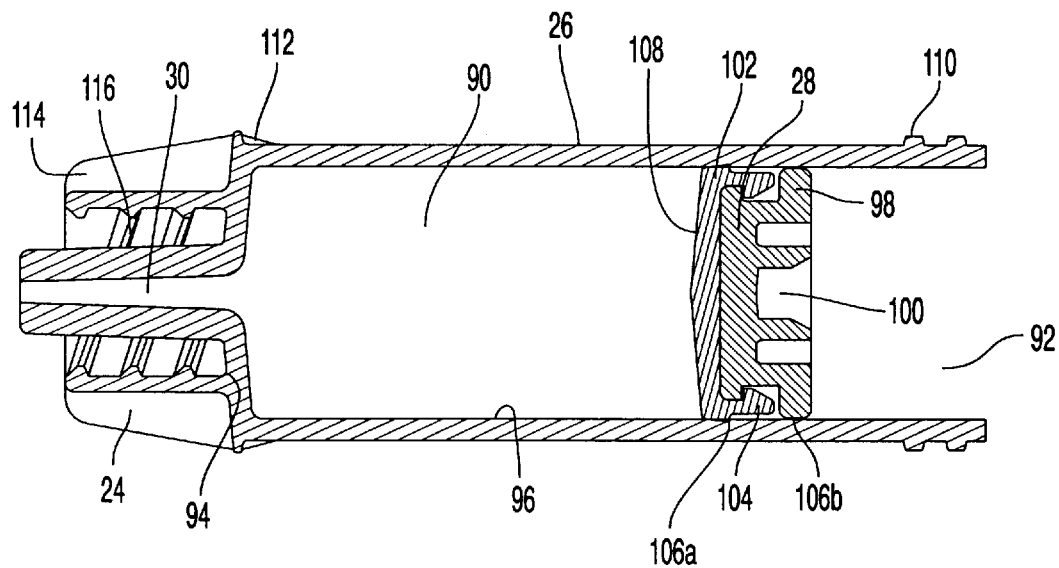
FIG. 6 is a cross-sectional view of the syringe pump.

FIG. 6 shows the details of syringe pump 26. Syringe pump 26 has a fluid-containing chamber 90. Fluid-containing chamber 90 includes an open first end 92, a second end 94 that has hole 30, and an interior wall 96 disposed between first end 92 and second end 94. It is the movement of plunger 28 in the direction from first end 92 to second end 94 that forces the fluid out hole 30. Plunger 28 is shown comprised of a top portion 98 engaged to power screw 84 at a recess 100 and a bottom portion 102. Top portion 98 is attached to bottom portion 102 by tab 104. Tab 104 is preferably configured so that no part of it contacts interior wall 96. Thus, plunger 28 only contacts interior wall 96 at zones 106a, 106b. In fact, if the tolerances between recess 100 and power screw 84 are sufficiently high, there is no contact at zone 106b. The minimization of the contact area between plunger 28 and interior wall 96 reduces the force necessary to move plunger 28 along interior wall 96 by reducing opposing frictional forces. Consequently, more of the force resulting from the change in length of shape memory element 38 provides the actuating force rather than being lost due to friction.

Syringe pump 26 has preferably been designed to minimize so-called "dead volume," the volume of fluid that remains in syringe pump 26 after plunger 28 has moved to second end 94. Specifically, lower surface 108 of bottom portion 102 is configured to be the "mirror image" of second end 94 such that when lower surface 108 contacts second end 94, substantially all fluid has been expelled from fluid-containing chamber 90.

The back of syringe pump 26 has threads 110 for connecting to micropump 10. Preferably, threads 110 are a double start acme thread. A seal 112 is made of pliable material such that as syringe pump 26 is screwed into micropump 10, the junction between the two is water-tight. Nozzle 24 has a finger grip 114 for facilitating insertion of syringe pump 26 into micropump 10. Nozzle 24 also has standard threaded Luer taper 116 for connection with industry-standard needle sets.

The manner in which a charge is applied to shape memory element 38 will now be described. FIG. 7 shows the top shell 14 having a lap joint 118 that together with lap joint 34 (FIG. 2) comprises the connection between top shell 14 and bottom shell 16. The connection can be made water-tight by a number of methods including ultrasonic welding, solvent bonding, or adhesive bonding. Battery 120 supplies electrical power to electronic control element 122. Electronic control element 122 is attached to top shell 14 by screws 124 and includes control knob 18 (FIG. 1), capacitors 126 for storing the charge and wires 40a and 40b for supplying shape memory element 38 with the charge. Electronic control element 122 also includes other conventional components that need not be discussed. Electronic control element 122 operates in such a manner that after a user-selectable time interval has passed, capacitors 126 release a user-selectable number of charges.

Referring again to FIG. 1, an optional battery isolation strip 128 is made of a nonconducting material and is positioned between battery 120 and electronic control element 122 such that battery isolation strip 128 must be removed by pulling in the direction of the arrow for battery 120 to provide electrical power to electronic control element 122. The user-selectable time interval and user-selectable number of charges are determined by control knob 18. Control knob 18 is shown as a six position switch. The marking "120 min" on the right hand side of control knob 18 indicates that the user-selectable time interval for the three positions on the right hand side of control knob 18 is 120 minutes. The marking "90 min" on the left hand side of control knob 18 indicates that the user-selectable time interval for the three positions on the left hand side of control knob 18 is 90 minutes. The first position on the right hand side of control knob 18, labelled "5 $\mu$l," indicates that the movement of plunger 28 induced by the charge causes approximately 5 $\mu$l to be expelled from hole 30 every 120 minutes. The other positions on the right hand side of control knob 18 are labelled "10 $\mu$l" and "20 $\mu$l." As these volumes are multiples of 5 $\mu$l and micropump 10 has been arranged such that one charge corresponds to approximately 5 $\mu$l, the desired volume is dispensed by the release of either two or four charges.

Although control knob 18 is shown in FIG. 1 as a six position switch corresponding to two user-selectable times of 90 or 120 minutes and 3 user-selectable volumes corresponding to 1, 2, or 4 charges, control knob 18 and electronic control element 122 can be arranged so that control knob 18 is any multiple position switch with each position corresponding to a different user-selectable times and number of charges.

While it is apparent that the illustrative embodiments of the invention herein disclosed fulfil the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

What is claimed is:

1. An apparatus for delivery of a fluid comprising:
   a syringe pump having a fluid-containing chamber, with an opening at a first end and a hole at a second end, and a plunger dimensioned for slidable engagement within the chamber such that when the plunger is acted upon by an activating force, the movement of the plunger from the opening towards the hole causes the fluid to be expelled from the chamber through the hole;
   an electronic control element releasing at least one charge at predetermined time intervals;
   a power source for providing electrical energy to the electronic control element;
   a shape memory element connected to the electronic control element in such a manner to form an electric circuit, said shape memory element having a changeable length decreasing from a uncharged length to a charged length when the at least one charge is applied to the shape memory element and, under force of a return element, returning to the uncharged length when the at least one charge is removed; and
   a driving mechanism connecting the shape memory element and the plunger such that the changeable length decreasing from the uncharged length to the charged length causes the driving mechanism to provide the activating force for movement of the plunger and expulsion of the fluid from the syringe pump chamber.

2. The apparatus of claim 1, wherein the chamber has an interior wall and the plunger has a top end connected to the driving mechanism, a bottom end configured such that when the bottom end contacts the second end of the chamber, substantially all fluid has been expelled from the chamber through the hole, and a side surface containing at least one seal member such that the plunger slidable engagement within the chamber involves contact only between the chamber interior wall and the at least one seal member.

3. The apparatus of claim 1, wherein the syringe pump chamber is made of an injection molded thermoplastic polymer and the shape memory element is made of a nickel-titanium alloy.

4. The apparatus of claim 1, wherein the power source is at least one battery and the electronic control element includes at least one capacitor for storing and releasing the at least one charge.

5. The apparatus of claim 1, wherein the electronic control element includes a time element for allowing the user to select a number of charges to be released and an interval at which the charges are released.

6. The apparatus of claim 1, further comprising a housing for retaining all components therein.

7. The apparatus of claim 6, wherein the housing includes a window to facilitate monitoring of the amount of fluid in the syringe pump.

8. The apparatus of claim 1, wherein the driving mechanism comprises:
- a power screw attached to the plunger such that longitudinal movement of the power screw provides the activating force; and
- a fixed nut through which the power screw is threaded such that rotation of the power screw through the nut results in the longitudinal movement of the power screw.

9. The apparatus of claim 8, wherein the driving mechanism further comprises a coupler for initiating the rotation of the power screw, the coupler having a bore for receiving the power screw configured and dimensioned such that the coupler and power screw rotate together.

10. The apparatus of claim 9, wherein the power screw has two threadless flat parallel surfaces and two threaded curved surfaces and the bore has two threadless flat parallel surfaces engaging the flat surfaces of the power screw.

11. The apparatus of claim 9, wherein the driving mechanism further comprises a pawl having a first end attached to the shape memory element and a second end contacting the coupler, the pawl moving from a resting position when the shape memory element has the uncharged length to an actuating position when the shape memory element has the charged length, said second end and coupler configured such that movement of the pawl causes the coupler to initiate the rotation of the power screw.

12. The apparatus of claim 11 wherein the return element comprises a return spring attached to the pawl to cause the pawl to return to the resting position.

13. The apparatus of claim 11, wherein the driving mechanism further comprises a limiting switch for stopping the at least one charge when the pawl moves past the actuating position and a projection on the first end of the pawl for engaging the limiting switch when the pawl moves past the actuating position.

14. The apparatus of claim 11, wherein the first end of the pawl has a channel to which the shape memory element is secured and the second end has an extension with a tab that engages a ratchet on an external surface of the coupler to initiate the rotation of the coupler.

15. The apparatus of claim 14, wherein a spring strip ratchet engages teeth of the ratchet to permit rotation of the coupler in one direction only.

16. The apparatus of claim 14, wherein the external surface of the coupler has a portion for manual rotation of the coupler.

* * * * *